United States Patent
Ballinger, Jr. et al.

(12) 
(10) Patent No.: US 7,488,493 B2
(45) Date of Patent: Feb. 10, 2009

(54) PERFORMANCE AID FOR PESTICIDE OR REPELLENT COMPOSITIONS

(75) Inventors: Kenneth E. Ballinger, Jr., Kennett Square, PA (US); Michele Santer, Wilmington, DE (US)

(73) Assignee: Arkion Life Sciences, LLC, Wilmington, DE (US)

( * ) Notice: Subject to any disclaimer, the term of this patent is extended or adjusted under 35 U.S.C. 154(b) by 861 days.

(21) Appl. No.: 10/831,260

(22) Filed: Apr. 23, 2004

(65) Prior Publication Data

US 2005/0019360 A1 Jan. 27, 2005

Related U.S. Application Data

(60) Provisional application No. 60/487,356, filed on Jul. 15, 2003.

(51) Int. Cl.
*A01N 25/04* (2006.01)

(52) U.S. Cl. .......................... 424/405; 514/680

(58) Field of Classification Search ........................ None
See application file for complete search history.

(56) References Cited

U.S. PATENT DOCUMENTS

| | | | |
|---|---|---|---|
| 3,663,253 A | 5/1972 | Stone | |
| 3,935,305 A | 1/1976 | Delaney et al. | |
| 5,106,872 A * | 4/1992 | Alder et al. | 514/587 |
| 5,296,226 A * | 3/1994 | Askham | 424/405 |
| 5,372,806 A * | 12/1994 | Holloway | 424/70.1 |
| 5,885,604 A | 3/1999 | Ballinger, Jr. | |
| 5,922,774 A | 7/1999 | Winslow | |
| 6,054,454 A | 4/2000 | Schmid et al. | |
| RE37,313 E | 8/2001 | Roberts | |
| 6,328,986 B1 | 12/2001 | Ballinger, Jr. | |
| 6,436,423 B1 | 8/2002 | Ballinger, Jr. | |
| 6,566,308 B1 | 5/2003 | Aven | |
| 6,576,223 B2 | 6/2003 | Runkel | |
| 6,582,712 B2 | 6/2003 | Pullen | |
| 6,642,178 B2 | 11/2003 | Woznica et al. | |
| 6,689,720 B2 | 2/2004 | Woznica et al. | |

* cited by examiner

*Primary Examiner*—Neil Levy
(74) *Attorney, Agent, or Firm*—McCarter & English

(57) ABSTRACT

A performance aid for increasing the effectiveness of a bioactive agent, and a composition including both the performance and the bioactive agent. The performance aid increases the effectiveness of the bioactive agent by providing a composition that adheres well to a surface but also increases transferability of the bioactive agent to a target animal that contacts the treated surface.

3 Claims, 1 Drawing Sheet

| | Baseline | 8-Apr | 9-Apr | 10-Apr | 11-Apr | 12-Apr | 13-Apr | 14-Apr |
|---|---|---|---|---|---|---|---|---|
| FC | 19.66% | 46.15% | 40.21% | 43.66% | 43.56% | 43.13% | 64.86% | 71.02% |
| S1 | 14.92% | 30.30% | 56.11% | 39.69% | 92.68% | 95.00% | 96.88% | 94.35% |

PERFORMANCE AID FOR PESTICIDE OR REPELLENT COMPOSITIONS

CROSS-REFERENCE TO RELATED APPLICATIONS

This application claims the benefit of U.S. Provisional Application No. 60/487,356, filed Jul. 15, 2003, the contents of which are incorporated herein by reference.

FIELD OF THE INVENTION

The invention relates to pesticides, repellents and other bioactive agents for controlling animals. More particularly, it relates to performance aid compositions effective in improving the effectiveness of such bioactive agents by increasing their uptake by the targeted animals.

BACKGROUND OF THE INVENTION

Pesticides are designed to be effective when the target is either feeding or in contact with a compound that can be transdermal in its effect. Chemical pesticides have been known and used for years. More recently, biopesticides have been introduced that exhibit parasitic or infective control of a number of species. Effectiveness is generally measured by the power of a pesticide to lower a pest population through lethal control.

Adjuvants are presently used in the industry to enhance or modify the chemical and/or physical characteristics of pesticides. Adjuvants generally have no pesticidal activity of their own. Because of the importance of spray application of pesticides, the use of adjuvants reduces application problems such as chemical stability, incompatibility, solubility, suspension, foaming, drift, evaporation, volatilization, phytotoxicity, surface tension, droplet size and coverage. Adjuvants can, depending upon their type, enhance wetting, spreading, sticking, emulsifying, and dispersing.

A new mode of pest control is growing in use wherein pests are managed by translocation or repellency rather than by lethal measures. This approach provides the advantage of reducing the probability of adaptation by the target species. In particular, because the target is not killed, the probability of two resistant individuals finding each other and mating is significantly reduced to the random probability of the genetic variant. Additional benefits of repellency include maintenance of the ecological balance in the location of use without the negative effect of the pest. Thus in some situations, repellency is a preferred method of long-term pest management.

Repellents are often targeted against a narrow list of target pests, under rather specific application conditions. For example, the compound 9,10-anthraquinone is known to be a powerful antifeedant for bird species. Birds will not feed on seed that contains as little as 0.1% 9,10-anthraquinone by weight. The lower limit of detection in birds is as low as 125 ppm, which is the threshold where birds begin to sense the repellency. Thus the presence of 9,10-anthraquinone is known to prevent birds from eating a material that the bird might otherwise consume.

It may also be desirable in some circumstances to prevent, in a non-lethal manner, a bird from occupying or roosting on a specific site, and means for doing this in a non-lethal manner are much sought after. Pigeons are routinely killed in cities to counter the health and maintenance problems created by their feces, but it is frequently preferable to merely drive the birds away. U.S. Pat. No. 6,328,986 provides a method for deterring birds from roosting or perching on plant and structural surfaces.

There is a need, however, for a performance aid that increases the transferability of the active compound from the applied surface to the pest animal of interest, while also remaining adhered to the surface.

If a coating could be created that would be easy to apply, nontoxic to animals and humans and have increased repellent characteristics, pest animal populations could be kept at a tolerable level without resorting to lethal population control. Thus there is a need for a more efficient, non-toxic, non-lethal means of repelling pest animals from designated areas.

SUMMARY OF THE INVENTION

In one aspect, the invention is an enhanced bioactive agent comprising an effective amount of a bioactive agent selected from the group consisting of pesticides, repellents, agricultural chemicals, biological agents, hormones and pheromes, and about 10%-99% of a performance aid, said performance aid comprising an effective combination of oil and at least about 10% salt water.

In another aspect, the invention is a method comprising:
a) forming an enhanced bioactive agent mixture comprising an effective amount of a bioactive agent selected from the group consisting of pesticides, repellents, agricultural chemicals, biological agents, hormones and pheromes, and about 10%-99% of a performance aid, said performance aid comprising an effective combination of oil and at least about 10% salt water; and
b) applying said enhanced bioactive agent mixture to a surface to form the treated surface.

In yet another aspect, the invention is a method comprising:
a) forming a performance aid comprising an effective combination of oil and at least about 10% salt water;
b) applying an effective amount of said performance on a surface;
c) applying an effective amount of a bioactive agent to said surface wherein said bioactive agent is selected from the group consisting of pesticides, repellents, agricultural chemicals, biological agents, hormones and pheromes.

In an additional aspect, the invention is directed to a composition comprising an effective amount of a low molecular weight carboxylic acid potassium salt, a vegetable oil, water and a bioactive agent selected from the group consisting of pesticides, repellents, agricultural chemicals, biological agents, hormones and pheromes.

In a final aspect, the invention is directed to a composition comprising an effective amount of a low molecular weight carboxylic acid potassium salt, a vegetable oil, and water.

DETAILED DESCRIPTION OF THE INVENTION

Figure 1:
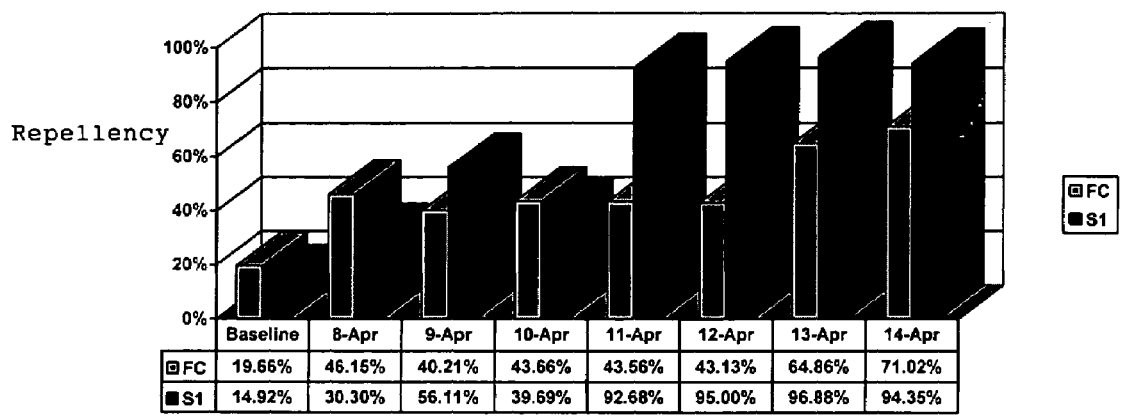
FIG. 1 is a bar graph depicting the percentage of bird repellency between repellent product alone and repellent product in a formulation of the invention.

The present invention provides a performance aid that when combined with a bioactive agent is capable of increasing transfer of that bioactive agent from a treated surface to an animal and thus increasing the effectiveness of the agent, without a need for the animal to purposely eat the material treated with the bioactive agent. As defined herein, the term "bioactive agent" means a material that affects the behavior and/or a biological function of an animal. While suitable bioactive agents are discussed in detail later in this document, some non-limiting examples include pesticides, repellents, agricultural chemicals, biological agents (for example a fungus or other organism), hormones, or pheromones. As used herein, the term "animal" is to be understood to include any member of the animal kingdom, including, but not limited to, birds, rodents, and insects.

Performance Aid

The performance aid according to the invention preferably comprises, in its most basic form, an oil combined with salt and water. The performance aid of the invention should preferably be capable of adhering well to the surface onto which it is applied. That being said, however, it is equally important that the performance aid also be capable of increasing transfer of a bioactive agent mixed therein to an animal that makes contact with the surface onto which the performance aid is applied. An inventive feature of the performance aid is that it both adheres well to the applied surface while retaining a certain amount of tackiness to increase transferability of the bioactive agent from the surface to an animal.

In very general terms, the performance aid of the invention preferably comprises at least 10%-15% salt water. Regarding the oil, while there is no requirement as to how much oil the performance aid should comprise, it is important that there at least be some amount of oil, and preferably, at least enough to coat the surface onto which it is being applied. In a preferred embodiment, the formulation of the performance comprises 60% oil and 40% salt. Regarding the salt water, generally it is preferred that the salt and water be in equivalent amounts (i.e. 50/50).

Oil

The oil may comprise any of a variety of nonvolatile liquids known in the chemical art, including but not limited to fatty acids, esterified fatty aids, saponified fatty acids, N,N-dimethylamides, polybutenes, and agricultural spray oils, all of which are described and defined in U.S. Pat. No. RE37,313, incorporated herein by reference, or mixtures of these. The oil preferred in this invention is a vegetable oil comprising one or more vegetable seed oils, as the term is understood in the agricultural industry, and/or a crop seed oil named for the particular crop from which it is produced. Suitable exemplary oils are cotton seed oil, canola oil, rapeseed oil, peanut oil, sunflower oil, linseed oil, safflower oil, soybean oil, corn oil, olive oil, coconut oil, tall oil or other seed oils and blends of the above oils.

Salt Water

Salt is preferably incorporated into the performance aid of the invention because it tends to act as a humectant that can maintain moisture within a certain range by either shedding water in moist conditions or absorbing moisture from the atmosphere in dry conditions. This ability to act as a humectant provides one means for causing the performance aid to remain tacky after application to a surface.

The salt is preferably an alkali metal or ammonium salt of a low molecular weight carboxylic acid. The salt of a low molecular weight carboxylic acid may comprise a salt of a C1-C18 mono- or polycarboxylic acid, which may be one or more of an aliphatic, aromatic, or combined aliphatic/aromatic acid or polyacid. In a preferred embodiment of the invention, the salt comprises a salt of a C1-C5 carboxylic acid, for example potassium acetate.

It is preferred that water be mixed with the salt. Water added to the salt forms a blend that lowers viscosity and as such, assists in the application of the product by allowing for spraying on remote locations such as hard to reach ledges and cornices. Alternatively, solvents such as alcohols or alcohol mixtures could be used in place of or, more preferably, in addition to water, where, for instance, fast drying may be required. Also, while the salt already depresses the freezing point of the performance aid to some degree, the use of alcohol mixtures would assist in further lowering the freezing point to allow the performance aid to remain effective in extremely cold conditions.

Generally, it is contemplated that virtually any non-toxic humectant as known by those having skill in the art (e.g. glycerol), would be effective in the invention so long as the humectant of choice is effective in maintaining a moisture content within the performance aid.

While it is preferred that the performance aid comprise equivalent amounts of the salt and water (i.e. 50/50), it is contemplated that performance aid formulations can be adjusted with regard to the salt and water to tailor the performance aid to properly suit the needs of a particular bioactive agent. For instance, as described in Example 1, the application used a 2:1 ratio of water to salt in the "S1" performance aid formulation. In this case, the additional water was incorporated to assist in the ease of application of the performance aid. As stated earlier, the most important effect of the water is to lower the viscosity, thus improving spray application capabilities where necessary.

Bioactive Agent

As described earlier, the term "bioactive agent", as used in this invention, is a material that affects the behavior and/or a biological function of an animal. Some non-limiting examples include pesticides, repellents, agricultural chemicals, biological agents (for example a fungus or other organism), hormones, or pheromones, among others.

Preferred bioactive agents for use in the invention include polycyclic quinone repellents. Certain polycyclic quinones, such as 9,10-anthraquinone, are known and used in the industry as bird repellents and are discussed in detail later in this document.

While polycyclic quinones are a preferred bioactive agent for use in the invention, it is contemplated that virtually any other bioactive agent can be used with the performance aid of the invention such that the transfer of such bioactive agent from the applied surface to the animal is increased. Some examples include insecticides such as organo-phosphates (e.g. Lindane) or carbamates (e.g. Mesurol® (Gowan, Yuma, Ariz.). Also included would be certain contact poisons where the animal would need to make contact with the active ingredient in order to allow for the active ingredient to dwell on the skin or carapace in order to be effective, for example nerve toxins. Finally, systemic fungicides that generally require an oil based adjuvant to adhere to plant surfaces, could also be effective in this invention.

Performance Aid and Bioactive Agent ("Enhanced Bioactive Agent")

An aspect of the invention is to provide an enhanced bioactive agent. An "enhanced bioactive agent" as used herein means a formulation comprising the performance aid of this invention in combination with a bioactive agent. The enhanced bioactive agent is effective in that once applied to a surface, the result upon drying is an adherent coating with a tacky surface wherein the bioactive agent is readily transferable to the target animal upon contact. It will be appreciated that the exact ingredient proportions involved in making such a formulation will vary considerably, depending upon the particular bioactive agent to be used and the make up of the performance aid. It is important that the enhanced bioactive agent formulation results in a coating having an appropriate level of stickiness once the solvent (i.e. water, alcohol, etc.) has evaporated after application to a surface. The appropriate level can be defined by optimizing the mixture for use with a particular animal. While a general rule of thumb is that the performance aid should comprise at least 10%, and more preferably, 20% of the enhanced bioactive agent formulation, the performance aid can comprise as much as 99% or more of the enhanced bioactive agent formulation, so long as dispersed therein is an effective amount of the bioactive agent. The quantity of a bioactive agent will clearly vary for each enhanced bioactive agent formulation as each bioactive agent has a known effective dosage. As such, the only requirement as to the formulation of the enhanced bioactive agent is that it contain at least the minimum effective dosage of the bioactive agent. The remainder of the enhanced bioactive agent formulation will therefore comprise the performance aid.

Alternative formulations are contemplated depending on specific needs associated with the application of the enhanced-bioactive agent. Some examples of alternative formulations comprise the enhanced bioactive agent of the invention in combination with other solvents, additional water, surfactants, dispersants, thickeners, pH control agents, flow control agents, antifoam agents, antifreeze agents, wetting agents, suspending aids, antibacterial agents or other preservatives, and/or other materials known in the art. Those having skill in the art are familiar with applications that require any of the just listed materials.

Mixing of the performance aid and the bioactive agent may be performed in any sequence of mixing and diluting steps. For example, the performance aid and the bioactive agent may be pre-mixed and then diluted, or diluted and then mixed, or any other combination of steps. The final enhanced formulation has a percent non-volatiles content of between 1 and 75 wt %, for example between 5 and 25 wt %. The non-volatiles content will depend, inter alia, upon the type of application equipment chosen. Such equipment may be of any type known in the art, for example a sprayer, roller, or brush.

Regarding the application of the product to a surface, it is preferred that the enhanced bioactive agent be formulated to adhere to any solid surface, and, more particularly, to ledges, roof material, beams, window sills, rafters and any other surface where an animal may roost or otherwise spend time. It is a further aspect of this invention that the enhanced bioactive agent, once applied to a surface, has considerable resistance to deterioration of effectiveness caused by weather conditions and environmental exposure in general.

The performance aid of this invention is also characterized in that it provides a means of adhering the bioactive agent to the applied surface for an extended, effective period of time. For example, using the specific example of 9,10-anthraquinone repellent, applicants determined that the repellent, when combined with the performance aid in the preferred quantities recited above, was superior in its ability to adhere to the boards for an extended period as compared to 9,10-anthraquinone mixed with water only (see Examples).

Surfaces

The performance aid of the invention is generally directed at providing a useful means for applying a bioactive agent to a solid surface. "Solid surfaces" as used in this document include surfaces such as roofs, black top (i.e. streets, parking lots, airport runways, etc.), sidewalks, benches, ledges, buildings, and any other related solid surface where pests such as birds and insects may gather and/or feed. While solid surfaces are the primary target for application of the enhanced bioactive agent of the invention, the performance aid formulation is also applicable to plant and turf surfaces. In particular, the formulation of the performance aid is adapted to adhere to plant and turf surfaces in the same manner it adheres to solid surfaces.

Application

It is preferred that the bioactive agent and the performance aid be combined to form the enhanced bioactive agent prior to application in order to achieve consistent dispersement of the bioactive material throughout the applied material. Application onto solid surfaces can be accomplished by any known means of applying a liquid product onto a surface. In the case of small surfaces and surfaces prone to dripping, it is preferred that the product of the invention be applied by a brush or roller. In the case of larger surfaces, spray application is preferred.

In an alternative embodiment, the performance aid and the bioactive agent are applied to the surface separately. Preferably, one or more coatings of the performance aid is first applied to the surface. Thereafter, the bioactive agent is applied onto the surface. Various alternatives are contemplated, such as several alternating layers of performance aid and bioactive agent on top of each other. In specific situations not necessarily addressed in this document, those having skill in the art can readily determine the best and most effective way to apply the products of the invention.

Polycyclic Quinones

As described earlier, polycyclic quinines are a preferred class of repellents used in the invention. A wide variety of polycyclic quinones can be used in the invention. As used herein, the term "polycyclic quinone" refers to bicyclic, tricyclid and tetracyclic condensed ring quinones and hydroquinones, as well as precursors thereof. On the whole, the non-ionic polycyclic quinones and polycyclic hydroquinones (herein referred to collectively as "PCQ"s) have very low solubility in water at ambient temperatures. For use in the invention, it is preferred that such PCQs have a water solubility no higher than about 1,000 ppm, by weight.

However, as noted above, certain precursors of such PCQs can also be used in the invention, either combined with the relatively insoluble PCQs or by themselves. Such precursors are anionic salts of PCQs which are water soluble under alkaline anaerobic conditions. However, these materials are not stable and are easily converted to the insoluble quinone form upon exposure to air. Thus, when anionic PCQs are applied to plants and exposed to air, they are quickly changed to the water-insoluble, more active quinone form.

Among the water-insoluble PCQs that can be used in the invention are anthraquinone, 1,2-dihydroxy anthraquinone, 1,4-dihydroxy anthraquinone, naphthoquinone, anthrone(9, 10-dihydro-9-oxo-anthracene), 10-methylene-anthrone, phenanthrenequinone and the alkyl, alkoxy and amino derivatives of such quinones, 6,11-dioxo-1H-anthra[1,2-c]pyrazole, anthraquinone-1,2-naphthacridone, 7,12-dioxo-7,12-dihydroanthra[1,2-b]pyrazine, 1,2-benzanthraquinone, 2,7-dimethylanthraquinone, 2-methylanthraquinone, 3-methylanthraquinone, 1-aminoanthraquinone and 1-methoxyanthraquinone. In addition, more complex polycyclic quinone compounds can be used, such as 2-carboxy-1,3,5,6, 8-pentahydroxy-7-monosaccharide and other saccharides of anthraquinones or glucosamides and 2(1,3-dihydro-3-oxy-5-sulfo-2H-indol-2-ylidine)-2,3-dihydro-3-oxo-1H-indole-5-sulfonic acid, disodium salt. Of the foregoing cyclic ketones, anthraquinone and 1,4-dihydroxyanthraquinone are preferred because they appear to be more effective. Naturally occurring anthraquinones can be used as well as synthetic anthraquinones.

Other PCQs which can be used include insoluble anthraquinone compounds, such as 1,8-dihydroxy-anthraquinone, 1-amino-anthraquinone, 1-chloro-anthraquinone, 2-chloro-anthraquinone, 2-chloro-3-carboxyl-anthraquinone and 1-hydroxy-anthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9-10) will result in the formation of the insoluble molecular anthrahydroquinone. Aerobic solutions will incur oxidation of the anthraquinones to anthraquinone. Thus, anthrahydroquinones will not exist for long periods of time in an aerated environment, such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

The PCQ used should be in physical form small enough to be touched by the sensory organs of the bird. Thus, for the PCQ to be more effective as a repellent, it is preferred to be of sufficiently small particle size that its presence can be sensed. Thus, the more effective quantity of repellent in any application is that which is in a form accessible to the birds' nerve endings; that is, it should be of sufficiently small size that it can be orally sensed.

It is preferred that the polycyclic quinine, and in particular, 9,10-anthraquinone, be applied to the surface to be treated at a level ranging from 0.2 mg/sq meter to 1000 mg/sq meter of surface. It is more preferred that the polycyclic quinone be applied to the surface at a level ranging from 1 mg/sq meter to 50 mg/sq meter. It is most preferred that the polycyclic quinine be applied to the surface at a level ranging from 5 mg/sq meter to 25 mg/sq meter of surface to be treated.

In one exemplary embodiment of the invention, the performance aid is combined with a water-based slurry comprising 9,10-anthraquinone, a known repellent. The performance aid blends with the 9,10-anthraquinone. Although in some embodiments the 9,10-anthraquinone is in a solid form, such as a powder or granules, it may alternatively be dissolved in one or more other components of the performance aid. In one embodiment, the performance aid is mixed with the 9,10-anthraquinone slurry and then the combination is mixed to a dilution level suitable for use with any of a variety of types of application equipment. In one exemplary embodiment, the 9,10-anthraquinone slurry is a standard water based 50% slurry bird repellent formulation sold under the name Flight Control Plus® by Airepel LLC of Wilmington, Del. Once the adjuvant/repellent mixture is applied to a surface and the water evaporates, the 9,10-anthraquinone is bound in a sticky mixture that coats the treated surface, while at the same time, an effective amount of which transfers to an animal, such as a bird, when walked on.

It is preferred that the bioactive agent of this preferred composition, i.e. 9,10-anthraquinone, is efficiently transferred from the coated surface to the foot pad of a bird walking or perching thereon. Once transferred to the foot pad, the 9,10-anthraquinone is naturally then transferred from the foot pad to the feathers and then to the bill during normal preening activity. The oily nature of the performance aid makes the 9,10-anthraquinone stick better to the foot pads and feathers of the birds thus more effectively transferring greater quantities of the active agent from the treated surface to the bird. In addition, the use of the humectant (in this case the salt) allows the oil to remain soft and sticky while on the surface.

In this embodiment, a preferred ratio of 9,10-anthraquinone slurry (50% 9,10-anthraquinone and 50% water) to performance aid is 85% or less of 9,10-anthraquinone slurry and 15% or more of performance aid. In a more preferred embodiment, the enhanced bioactive agent comprises 75%-85% 9,10-anthraquinone slurry and 15%-25% or more performance aid, wherein the performance aid comprises 15%-20% oil, 1%-2% salt and 1%-2% water. In a most preferred embodiment, the enhanced bioactive agent comprises 30%-40% 9,10-anthraquinone slurry, and 60%-70% performance aid, wherein the performance aid comprises 30%-40% vegetable oil, 10%-20% salt and 10%-20% water.

Again referring specifically to the repellent 9,10-anthraquinone, without wishing to be bound by any particular theory or explanation, it is believed that once a bird has picked up 9,10-anthraquinone on the footpad, the 9,10-anthraquinone transfers to the feathers during the foot-to-feather preening behavior. Once the 9,10-anthraquinone is on the feathers, the bill encounters the 9,10-anthraquinone during feather preening behavior. It is further believed that 9,10-anthraquinone is thereby ingested in small quantities, giving the bird a gastric reaction that teaches the bird to avoid a roost site that has been treated with the formulation. Birds learn quickly to avoid 9,10-anthraquinone, and it is further believed that they are then warned away by the color of the product in UV and/or visible wavelengths, where 9,10-anthraquinone has significant spectral absorption.

In prior applications of 9,10-anthraquinone mixed with water to surfaces, such surfaces were dry and hard to the touch and released less 9,10-anthraquinone to the bird. The result was a lower repellency effect. As shown in the examples, the 9,10-anthraquinone and water mixture incorporated more 9,10-anthraquinone per square foot than the applications incorporating the performance aid of the invention, yet showed lower repellency. Further, the powdery residue of 9,10-anthraquinone on the harder surface did not adhere to the feathers as well as the residue from the performance aid enhanced formulations.

The advantageous properties of this invention can be observed by reference to the following examples which illustrate the invention.

EXAMPLES

Example 1

The following example demonstrates the enhanced effectiveness of two bird repellent compositions, designated made-down Flight Control Plus (FC+) and S1, comprising the adjuvants of the present invention for repelling rock doves (pigeons). The rock doves were captured from the wild and allowed to walk on boards in their cages. The boards were half covered with test material to evaluate the performance of different 9,10-anthraquinone formulations as a surface repellent. Details of the testing and results are shown below.

Housing and Maintenance of the Test Birds

Studies were conducted at the laboratory facility of Arkion Life Sciences LLC in Wilmington Del. in a dedicated facility that was prepared as an aviary. Eight bird cages were mounted on the wall. Each cage was designed for a single bird. Special floors were constructed for the cages to simulate painted metal roost sites. The floors of each cage were designed to have 2 sides, one having repellent thereon, the other having no repellent. Each side of the cage was labeled A and B. Food and water dishes were mounted on the cage sides at the mid point line to neutralize choice of either side.

Captive birds were fed a diet of cracked corn and mixed wild bird seed in an equal blend. Water and feed were available ad lib.

Pre-test Measurements

Birds were placed on boards with no test material on either side to allow an accommodation phase to new surroundings. Bird droppings were counted daily to determine bias for side A vs. side B. The pre-test period was used as a baseline measurement. Bird preference for the sides of the cages were influenced by attraction between birds caused by mating signals so every attempt was made to block visibility between cages. Regardless of the causes for attraction, the dropping counts were used as a measurement of the actual preference of the individual birds. Once a pattern of choice was apparent, birds were ready for testing.

Test Measurements

The untreated boards were removed from the cages at the beginning of a test period and treated boards were inserted. Each bird was exposed to test boards where one half of the board was painted with the repellent formulation and the other half remained untreated. Bird droppings were used to determine the choice made by the bird to occupy side A or side B of the cage. Droppings were counted daily and the data was used to determine the percentage of time the bird occupied side A or B. Occasional cage cleaning took place in order to maintain the health of the birds.

Repellency was expressed as a percent of the time the bird occupied side A or side B, the percent being derived from counts of bird droppings. Since birds leave droppings at a standard rate, dropping counts are an accurate measurement of the time a bird occupied a given side of the cage. The calculation used was:

Side Occupied % = $A/(A+B) \times 100$ where A and B represent droppings counts on sides A and B, respectively.

Test Formulations

Three tank mix versions of adjuvant formulations were used in the test. The repellent used was commercial Flight Control Plus® bird repellant (an anthraquinone (AQ) slurry comprising 50% active AQ and 50% inert ingredients). All materials used in the tank mix were food grade materials that were already listed by the U.S. Environmental Protection Agency as approved adjuvants for pesticides. The term "made-down Flight Control Plus®" is also designated as FC+ and refers to commercial, as-sold Flight Control Plus® that has been diluted to a concentration suitable for use, as shown in the table below.

| Designation | Flight Control Plus ® % | Tank Mix Components |
|---|---|---|
| FC+ | 50% | Water 50% |
| S1 | 78% | vegetable oil 19% potassium acetate 1% water 2% |

Preparation of Test Boards

For each floorboard, the test half of the board was painted with the treatment formulation. Four boards were used, each of which had ½ of their surface coated with repellent. The other half was not treated with repellent. Two boards were coated with standard made-down Flight Control Plus® and the other two boards were coated with S1. The repellent formulations were applied to their half of each board in the concentrations set forth below in Table 1.

TABLE 1

| Test Bird | Formulation | Amount Applied |
|---|---|---|
| Ardencroft | FC+ | 101.0 g. |
| Axelrod | FC+ | 98.8 g. |
| America | S1 | 61.4 g. |
| Atlas | S1 | 60.9 g. |

Test Data

Four wild rock doves named Ardencroft, Axelrod, America and Atlas, were placed in their cages on Apr. 7th, 2003. The birds were allowed to acclimate to their surroundings on untreated test boards for one day. Baseline measurements of their droppings were made to determine side preference. Test boards were inserted at on April 8th. Droppings were counted and time of day noted until the test period ended on April 14th. The choice of which side would be treated with a repellent formulation was made by coin toss.

Birds were photographed and filmed on April 8th to monitor behavior at introduction to the formulations. The two birds exposed to FC+ (Ardencroft and Axelrod) were observed walking liberally on the treated surface with no apparent change in behavior. The two birds walking on the S1 treated surface (America and Atlas) were observed tracking the compound onto the untreated side of the cage. On April 8th, all birds were observed for the presence of compound on their bodies. America was observed to have a small spot (<1 mm diameter) of S1 compound on her plumage at her shoulder. America and Atlas had S1 compound on their footpads. Ardencroft and Axelrod had FC+ compound under their talons and no compound was observed on their footpads.

The birds were observed again on April 9th for the presence of compound on their bodies. No compound was observed on any bird with the exception of S1 on the footpads of Atlas and America. Some FC+ compound remained in the talons of Ardencroft and Axelrod. The FC+ treated surfaces in Ardencroft and Axelrod's cages showed signs of scratches where their talons had broken through the painted surface. Atlas and America had no additional tracking of the S1 compound to the untreated side and seemed to be avoiding the S1 treated surfaces.

Birds were observed again on April 10th. Atlas and America had no observed S1 compound on their bodies. Axelrod and Ardencroft had FC+ compound on their talons. The decision was made to continue dropping counts until April 14th. Dropping counts are shown in Table 2, where shading indicates treatment on that side of the board.

TABLE 2

| America | | | | Axelrod | | | |
|---|---|---|---|---|---|---|---|
| Date | Time | Untreated | S1 Treated | Date | Time | Untreated | FC+ Treated |
| 7 Apr. 2003 | 1600 | 1 | 7 | 7 Apr. 2003 | 1600 | 1 | 12 |
| 8 Apr. 2003 | 850 | 2 | 8 | 8 Apr. 2003 | 850 | 14 | 12 |
| 8 Apr. 2003 | 1030 | | | 8 Apr. 2003 | 1030 | | |
| 8 Apr. 2003 | 1210 | 2 | 3 | 8 Apr. 2003 | 1210 | 3 | 0 |
| 8 Apr. 2003 | 1710 | 6 | 3 | 8 Apr. 2003 | 1710 | 9 | 1 |
| 9 Apr. 2003 | 1030 | 16 | 5 | 9 Apr. 2003 | 1030 | 21 | 12 |
| 9 Apr. 2003 | 1530 | 17 | 7 | 9 Apr. 2003 | 1530 | 29 | 12 |
| 10 Apr. 2003 | 1030 | 10 | 16 | 10 Apr. 2003 | 1030 | 31 | 12 |
| 11 Apr. 2003 | 1000 | 16 | 3 | 11 Apr. 2003 | 1000 | 17 | 5 |
| 11 Apr. 2003 | 1445 | 19 | 3 | 11 Apr. 2003 | 1445 | 19 | 5 |
| 12 Apr. 2003 | 920 | 8 | 0 | 12 Apr. 2003 | 920 | 18 | 5 |
| 13 Apr. 2003 | 1015 | 15 | 1 | 13 Apr. 2003 | 1015 | 37 | 8 |
| 14 Apr. 2003 | 815 | 23 | 1 | 14 Apr. 2003 | 815 | 45 | 8 |

| Atlas | | | | Ardencroft | | | |
|---|---|---|---|---|---|---|---|
| Date | Time | S1 Treated | Untreated | Date | Time | Untreated | FC+ Treated |
| 7 Apr. 2003 | 1600 | 17 | 1 | 7 Apr. 2003 | 1600 | 0 | 16 |
| 8 Apr. 2003 | 850 | 29 | 8 | 8 Apr. 2003 | 850 | 4 | 25 |
| 8 Apr. 2003 | 1030 | | | 8 Apr. 2003 | 1030 | | |
| 8 Apr. 2003 | 1210 | 8 | 0 | 8 Apr. 2003 | 1210 | 0 | 7 |
| 8 Apr. 2003 | 1710 | 20 | 1 | 8 Apr. 2003 | 1710 | 0 | 14 |
| 9 Apr. 2003 | 1030 | 22 | 12 | 9 Apr. 2003 | 1030 | 4 | 29 |
| 9 Apr. 2003 | 1530 | 22 | 16 | 9 Apr. 2003 | 1530 | 5 | 32 |
| 10 Apr. 2003 | 1030 | 26 | 18 | 10 Apr. 2003 | 1030 | 7 | 39 |
| 11 Apr. 2003 | 1000 | 0 | 19 | 11 Apr. 2003 | 1000 | 1 | 23 |
| 11 Apr. 2003 | 1445 | 0 | 24 | 11 Apr. 2003 | 1445 | 1 | 34 |
| 12 Apr. 2003 | 920 | 1 | 9 | 12 Apr. 2003 | 920 | 2 | 23 |
| 13 Apr. 2003 | 1015 | 0 | 13 | 13 Apr. 2003 | 1015 | 19 | 21 |
| 14 Apr. 2003 | 815 | 2 | 26 | 14 Apr. 2003 | 815 | 28 | 21 |

Calculation of % side preference was made from the dropping counts in Table 2 as follows:

Side Occupied % = A/(A + B) × 100 where A and B represent dropping counts on sides A and B, respectively. Multiple dropping counts from a single day are averaged. The results are presented in Table 3.

America and Atlas were released on April 14th because it was apparent they were avoiding the side treated with the S1 formulation. Both birds were in apparent good health.

TABLE 3

| | No Treatment | Treatment | | No Treatment | Treatment |
|---|---|---|---|---|---|
| | America | | | Axelrod | |
| Baseline | 16.25% | 83.75% | Baseline | 32.42% | 67.58% |
| 8-Apr | 57.14% | 42.86% | 8-Apr | 92.31% | 7.69% |
| 9-Apr | 73.33% | 26.67% | 9-Apr | 67.57% | 32.43% |
| 10-Apr | 38.46% | 61.54% | 10-Apr | 72.09% | 27.91% |
| 11-Apr | 85.37% | 14.63% | 11-Apr | 83.72% | 16.28% |
| 12-Apr | 100.00% | 0.00% | 12-Apr | 78.26% | 21.74% |
| 13-Apr | 93.75% | 6.25% | 13-Apr | 82.22% | 17.78% |
| 14-Apr | 95.83% | 4.17% | 14-Apr | 84.91% | 15.09% |
| | Atlas | | | Ardencroft | |
| Baseline | 13.59% | 86.41% | Baseline | 6.90% | 93.10% |
| 8-Apr | 3.45% | 96.55% | 8-Apr | 0.00% | 100.00% |
| 9-Apr | 38.89% | 61.11% | 9-Apr | 12.86% | 87.14% |
| 10-Apr | 40.91% | 59.09% | 10-Apr | 15.22% | 84.78% |
| 11-Apr | 100.00% | 0.00% | 11-Apr | 3.39% | 96.61% |
| 12-Apr | 90.00% | 10.00% | 12-Apr | 8.00% | 92.00% |
| 13-Apr | 100.00% | 0.00% | 13-Apr | 47.50% | 52.50% |
| 14-Apr | 92.86% | 7.14% | 14-Apr | 57.14% | 42.86% |

Ardencroft and Axelrod continued to be observed. The same study set up was used again, only this time the treatment sides were reversed mid-study to challenge the birds to demonstrate signs of avoidance. Both birds were again tested with FC+. The study was run for six days, and results are shown in Table 4. Data collected multiple times in the same day were averaged for that day. The sides of the board representing the side treated with FC+ is designated by the shading.

TABLE 4

| Ardencroft | | | | Axelrod | | | |
|---|---|---|---|---|---|---|---|
| Date | Time | A | B | Date | Time | A | B |
| 15 Apr. 2003 | 915 | *1* | 27 | 15 Apr. 2003 | 915 | *7* | 23 |
| 16 Apr. 2003 | 845 | *3* | 40 | 16 Apr. 2003 | 845 | *14* | 35 |
| 16 Apr. 2003 | 1400 | *3* | 43 | 16 Apr. 2003 | 1400 | *28* | 38 |
| 17 Apr. 2003 | 1110 | 2 | *21* | 17 Apr. 2003 | 1110 | 16 | *10* |
| 18 Apr. 2003 | 1115 | 4 | *27* | 18 Apr. 2003 | 1115 | 25 | *10* |
| 19 Apr. 2003 | 1745 | 6 | *10* | 19 Apr. 2003 | 1745 | 16 | *13* |

A calculation was made of % side preference and as before, and the data is shown in Table 5 below.

TABLE 5

| | Ardencroft | | | Axelrod | |
|---|---|---|---|---|---|
| | No Treatment | Treatment | | No Treatment | Treatment |
| 15-Apr | 96% | 4% | 15-Apr | 76% | 23% |
| 16-Apr | 93% | 7% | 16-Apr | 62% | 38% |
| 17-Apr | 9% | 91% | 17-Apr | 62% | 38% |
| 18-Apr | 13% | 87% | 18-Apr | 71% | 29% |
| 19-Apr | 37% | 62% | 19-Apr | 55% | 45% |

Two new wild birds were placed in cages on untreated boards on April 16th. These birds were designated the "B" series and were given names. Becky was observed for 3 days and it was determined that her feces indicated she was not normal and she was promptly released. Bingo was introduced to S1 applied to the boards on April 21st at a rate of 25.77 grams for the 2.83 square feet on the test is half. The board was allowed to dry for 3 days before placing it under Bingo on April 23rd at 1630. Bingo was introduced to 3 day old S1 to see if a shorter drying time made a difference. The untreated sides were carefully scrubbed to remove any residues of S1. Dropping counts are shown below in Table 6. Shading is used to show droppings after the S1 treated board was put into place.

TABLE 6

| | | Bingo | S1 3 day | | | Becky | |
|---|---|---|---|---|---|---|---|
| | | A | B | | | A | B |
| 16 Apr. 2003 | 1110 | 8 | 15 | 16 Apr. 2003 | 1110 | 15 | 12 |
| 17 Apr. 2003 | 1115 | 27 | 19 | 17 Apr. 2003 | 1115 | 18 | 25 |
| 18 Apr. 2003 | 1745 | 40 | 30 | 18 Apr. 2003 | 1745 | 10 | 26 |
| 21 Apr. 2003 | 1213 | 25 | 27 | Test interrupted due to bird release | | | |
| 22 Apr. 2003 | 1145 | 1 | 13 | | | | |
| 23 Apr. 2003 | 1630 | 0 | 7 | | | | |
| | 935 | | 23 | | | | |
| 24 Apr. 2003 | 1115 | *0* | 2 | | | | |
| 25 Apr. 2003 | 1030 | *1* | 24 | | | | |
| 26 Apr. 2003 | 1010 | *0* | 35 | | | | |
| 27 Apr. 2003 | 1610 | *2* | 37 | | | | |
| 28 Apr. 2003 | 1115 | *2* | 46 | | | | |
| 29 Apr. 2003 | 1000 | *3* | 17 | | | | |
| 30 Apr. 2003 | | | | | | | |

The dropping count was converted to percent side preference shown in Table 7 below.

TABLE 7

| | Bingo | |
|---|---|---|
| | No Treatment | Treatment |
| Baseline | 52% | 48% |
| 24-Apr-03 | 100% | 0% |
| 25-Apr-03 | 67% | 33% |
| 26-Apr-03 | 100% | 0% |
| 27-Apr-03 | 100% | 0% |
| 28-Apr-03 | 95% | 5% |
| 29-Apr-03 | 96% | 4% |
| 30-Apr-03 | 85% | 15% |

Results and Discussion

The first four birds were collected on April 6th and allowed to accommodate for 24 hours on untreated boards. The boards were prepared 17 hours before the birds were exposed to the compound. The S1 treated boards had a very oily feel and compound easily came off onto a metal spatula as well as fingertip. Standard made-down Flight Control Plus®-treated boards had dried to a hard surface with no apparent compound removed by spatula or fingertip.

Birds on S1 were observed tracking compound onto the untreated side and compound was noted on the birds within two hours of exposure. Within 3 days, the S1 birds had selected the untreated side and no compound was visible on the feathers. It is assumed the birds had preened the compound off since there was no bathing capability in the cages. The made-down Flight Control Plus®-treated birds had no visible compound on their feathers but some compound was seen on their talons. The surface of the made-down Flight Control Plus®-treated boards showed signs of indentations caused by the bird's feet.

It was observed that the two birds were not tracking compound as readily because the surface of the older S1 compound had dried to the point that its tactile feel was similar to that of the standard made-down Flight Control Plus®. Observations of the birds indicated that Bingo was tracking some compound onto the untreated side on April 24th.

The first round of testing revealed a marked difference in repellency between the made-down Flight Control Plus®, (FC+), and the mixture of Flight Control Plus® and adjuvant, (S1). Day three showed strong repellency with S1 compared to FC+.

FIG. 1 reflects averaging of the side preference % data of Atlas and America, and of Ardencroft and Axelrod. The oil based adjuvant used in formulation S1 of this experiment provided improved performance versus made-down Flight Control Plus®.

The oil based S1 adjuvant used in this experiment improved the repellency performance for Flight Control Plus® over the made-down Flight Control Plus® formulation. S1 made the anthraquinone (AQ) more available to birds upon contact. Fast repellency is one way to limit the birds' exposure time to the compound and drive them away. S1 contained 28% less AQ than what was in FC+ yet showed better repellency. The food grade vegetable oil used in the adjuvant is not a bird repellent and is routinely found in vegetables and seeds normally eaten by birds. The increased repellency by the S1 formulation demonstrated that the AQ was better transferred to the bird, thus resulting in better repellency.

Example 2

This Example demonstrates the enhanced effectiveness of a preferred adjuvant formulation "S2" over the S1 formulation used in Example 1. The S2 compound was tested successfully on the remaining three birds from Example 1, i.e. Axelrod, Ardencroft and Bingo. Three boards were prepared and painted on May 3rd. New treatment compound S2 was prepared according to the formulation shown below in Table 8.

TABLE 8

| Designation | Flight Control Plus ® % | Tank Mix Components |
|---|---|---|
| S2 | 34% | vegetable oil 34% potassium acetate 16% water 16% |

Three boards were used, each of which had ½ of their surface coated with S2. The other half was not treated. The S2 was applied in the concentrations set forth below in Table 9.

TABLE 9

| Test Bird | Formulation | Amount Applied |
|---|---|---|
| Axelrod | S2 | 37.5 g. |
| Ardencroft | S2 | 37.0 g. |
| Bingo | S2 | 30.3 g. |

Dropping counts were made to test the effectiveness of the S2 formulation. The baseline was calculated as the average dropping count of the previous four days. All birds picked up S2 on their footpads on first contact and they tracked material onto the untreated surface. The presence of S2 was noted on the feathers of all three birds within 2 hours of exposure. Axelrod and Bingo were observed to decrease their total dropping counts during the last two days of the trial. Axelrod accumulated repellent on the ventral side of the tail feathers on May 7th during frequent excursions onto the treated side. Both Ardencroft and Bingo tended to stay on untreated Side A. Axelrod at first preferred to stay close to the other birds on side A, even though it was treated. The following day, however, Axelrod left side A and he apparently ceased feeding, based on the dropping count decrease. All birds were released on the morning of May 8th after recording the dropping count, which is set forth in Table 10 below.

TABLE 10

| | Axelrod on S2 | | | Ardencroft on S2 | |
|---|---|---|---|---|---|
| | A | B | | A | B |
| Baseline | 11 | 15 | Baseline | 9.7 | 14.7 |
| 3 May 2003 | 935 | 0 | 12 | 3 May 2003 | 1100 | 8 | 1 |
| 4 May 2003 | 1115 | 1 | 17 | 4 May 2003 | 829 | 17 | 2 |
| 5 May 2003 | 1030 | 4 | 27 | 5 May 2003 | 930 | 28 | 5 |
| 6 May 2003 | 1010 | 5 | 33 | 6 May 2003 | 845 | 21 | 0 |
| 7 May 2003 | 1605 | 5 | 4 | 7 May 2003 | 1355 | 7 | 0 |
| 8 May 2003 | 1115 | 1 | 5 | 8 May 2003 | 855 | 15 | 0 |

| | Bingo on S2 | |
|---|---|---|
| | A | B |
| Baseline | 2 | 33 |
| 3 May 2003 | 1100 | 11 | 4 |
| 4 May 2003 | 830 | 26 | 4 |
| 5 May 2003 | 930 | 35 | 9 |
| 6 May 2003 | 845 | 41 | 6 |
| 7 May 2003 | 1355 | 15 | 0 |
| 8 May 2003 | 855 | 7 | 0 |

Results and Discussion

All birds reversed their accustomed sides measured in the baseline.

The S2 formulation allowed for a reduction in the concentration of Flight Control Plus in the final application from approximately 78% to approximately 34%. The S2 mixture was considerably more oily to the touch and was made with the intent to keep it from drying out over time.

Figure 2:
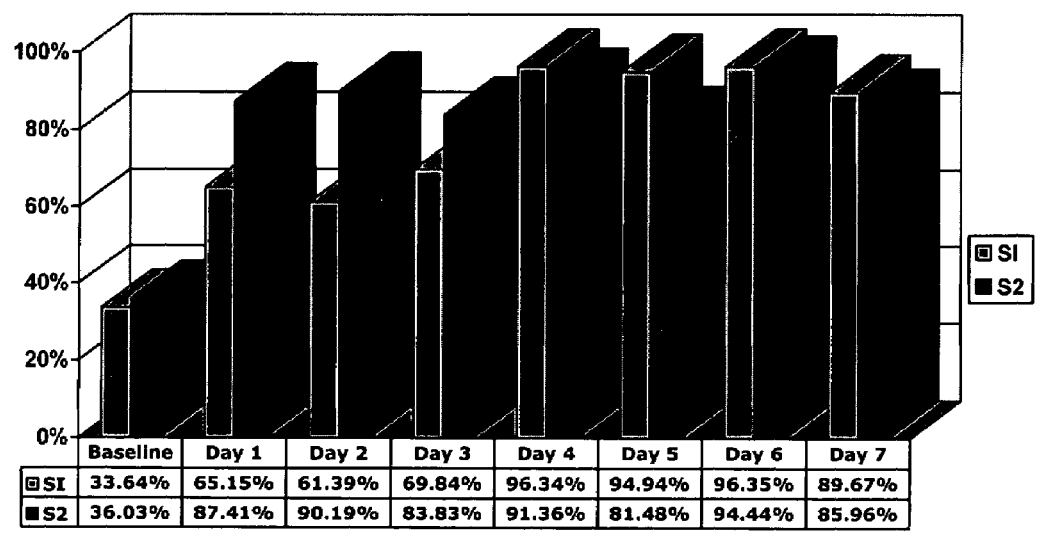
FIG. 2 is a bar graph depicting the percentage of bird repellency effectiveness between two formulations of the invention.

S2 showed a faster repellency compared to S1 and achieved the objective of forcing three birds to avoid the surface within the first 24 hours of exposure (see FIG. 2). Ardencroft and Axelrod had not shown any aversion to the compound until they were introduced to S2.

The oil based S2 adjuvant used in this experiment improved the performance for Flight Control Plus over that of the S1 formulation. S2 clearly made the AQ more available to birds upon contact. In addition, S2 contained less than half the AQ that was in S1 yet showed faster repellency. As described in Example 1, the food grade vegetable oil used in the adjuvant is not a bird repellent and is routinely found in vegetables and seeds normally eaten by birds. The fast repellency of the higher oil concentration demonstrated that birds spread AQ rapidly into feathers and preened the material within hours of contact.

Birds caged in close proximity to treated surfaces have very little room to avoid the compound. To make a bird change roosting behavior and switch sides of the cage is a testament to the power of the repellent. Flight Control Plus is an effective surface repellent for rock doves. This study documents new ways to enhance performance and shows ways to use minimum amounts of AQ to achieve rapid repellency.

Example 3

This study was conducted at Monica's wheat meal plant in Puerto Cabello, Carabobo State, Venezuela. The plant has a severe problem with over 150 birds (pigeons) regularly roosting on its roofs. Applicants tested various concentrations of the S2 formulation, prepared as described above in Example 2, on sections of the roof to determine efficacy in repelling the pigeons.

The repellent used in this Example was the same as above, i.e. commercial Flight Control Plus® bird repellant (an anthraquinone (AQ) slurry comprising 50% active AQ and 50% inert ingredients) denoted as FC+.

The treatment applications were as follows:

T1: 1 liter of FC+ and 1 liter of S2 per 100 square meters.
T2: 2 liters of FC+ and 2 liters of S2 per 100 square meters.
T3: 0.8 liters of FC+ and 0.8 liters of S2 per 100 square meters.

The formulations were applied as described above and were tested for bird repellency over a period of 60 days. Results were calculated based upon dropping counts over those 60 days and are set forth in Table 13 below:

TABLE 13

| Treatment | FC+ per 100 sq. meters | S2 per 100 sq. meters | % Bird Repellency |
| --- | --- | --- | --- |
| T1 | 1 Liter | 1 Liter | 98% |
| T2 | 2 Liters | 2 Liters | 100% |
| T3 | 0.8 Liters | 0.8 Liters | *50% |
| T4 | 0 | 0 | 0% |

*Only effective for first 14 days

Interestingly, in the last 14 days of the study, while it rained quite heavily over certain periods during those two weeks, the above formulations remained adhered to the surface and continued to be effective in repelling the pigeons.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An enhanced bioactive agent comprising an effective amount of a bioactive agent wherein the bioactive agent comprises approximately 10%-20% 9,10-anthraquinone and approximately 60%-70% performance aid, said performance aid comprising an effective combination of approximately 30%-40% oil and approximately 10%-20% salt and approximately 10%-20% water, and wherein the salt comprises potassium acetate.

2. The enhanced bioactive agent of claim 1 wherein the oil is selected from the group consisting of cotton seed oil, canola oil, rapeseed oil, peanut oil, sunflower oil, linseed oil, safflower oil, soybean oil, corn oil, olive oil, coconut oil, tall oil, and any blends thereof.

3. The enhanced bioactive agent of claim 1, further comprising an alcohol.